United States Patent [19]

Bloy et al.

[11] Patent Number: 5,478,821
[45] Date of Patent: Dec. 26, 1995

[54] METHOD OF ACCELERATING THE PROLIFERATION OF EMDOTHELIAL CELLS WITH INHIBITION OF NO SYNTHASES

[75] Inventors: Christian Bloy, Paris; Jean-Pierre Cazenave, Strasbourg Cedex; Bernard Hercelin, Clermont; Bernard Teisseire, Paris, all of France

[73] Assignee: Roussel UCLAF, France

[21] Appl. No.: 269,648

[22] Filed: Jun. 30, 1994

[30] Foreign Application Priority Data

Jul. 2, 1993 [FR] France .................... 93 08111

[51] Int. Cl.$^6$ .................... A61K 31/175; A61K 31/165; A61K 31/12
[52] U.S. Cl. .................... 514/210; 514/12
[58] Field of Search .................... 514/210

[56] References Cited

U.S. PATENT DOCUMENTS 3,758,520  9/1973  Beaudet .

FOREIGN PATENT DOCUMENTS 401460  10/1994  European Pat. Off. .
924A  11/1961  France .

OTHER PUBLICATIONS

M. Ploin, "Etioven 10 mg., Medicament De L'annee", *La Gazette Medicale*, vol. 100, No. 20, p. 30, May 1993.
Laborit et al, "Effets de la Mono–Semicarbazone . . . Hemorragique Experimental", *Agressologie*, vol. 12, pp. 25–30, (1971).

*Primary Examiner*—Arthur C. Prescott
*Attorney, Agent, or Firm*—Bierman and Muserlian

[57] ABSTRACT

A method of accelerating the proliferation of endothelial cells with inhibition of NO synthases in warm-blooded animals comprising administering to warm-blooded animals an amount of at least one compound selected from the group consisting of a β-naphthoquinone of the formula

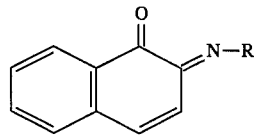

wherein R is selected from the group consisting of —NH—CO—NH$_2$, —NH—CO—CH$_3$ and —OH and their nontoxic, pharmaceutically acceptable acid addition salts in an amount sufficient to accelerate the proliferation of endothelial cells.

5 Claims, No Drawings

METHOD OF ACCELERATING THE PROLIFERATION OF EMDOTHELIAL CELLS WITH INHIBITION OF NO SYNTHASES

STATE OF THE ART

French Special Medicament Patent No. 924 M describes the use as medicaments of β-naphthoquinone derivatives wherein these derivatives are presented as having hemostatic properties and vitamin properties. It is known that the endothelium is constituted by a monolayer of cells of mesodermic origin which line the inside of the whole vascular system. Therefore, it constitutes the interface between the blood and the neighbouring tissues and this localization gives it a major role in the maintenance of vascular and blood integrity.

Detachment of the non-thrombogenic endothelial cells of the monolayer leads to exposure of the thrombogenic sub-endothelium (platelet and leukocytic adhesion). Exposure of the sub-endothelium is a pathological situation which is found in certain surgical interventions: embolectomies, angioplasties, endarterectomies and transplants of vascular protheses or in certain medical pathological situations (atherosclerosis, vascularitis). All these situations have a common interest which is the rapid reconstitution of an intact and functional endothelial surface. It has been recently demonstrated that the polypeptide growth factors (FGF: fibroblast growth factor; PDGF: platelet derived growth factor or EGF: epidermal growth factor) play an important role in the repair of vascular or cutaneous lesions: ulcers, eschars and burns.

OBJECTS OF THE INVENTION

It is an object of the invention to provide a novel method of accelerating endothelial cell proliferation and inhibiting NO synthases.

This and other objects and advantages of the invention will become obvious from the following detailed description.

THE INVENTION

The novel method of the invention of accelerating the proliferation of endothelial cells with inhibition of NO synthases in warm-blooded animals comprises administering to warm-blooded animals an amount of at least one compound selected from the group consisting of a β-naphthoquinone of the formula

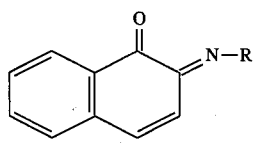

wherein R is selected from the group consisting of —NH—CO—NH$_2$, —NH—CO—CH$_3$ and —OH and their non-toxic, pharmaceutically acceptable acid addition salts in an amount sufficient to accelerate the proliferation of endothelial cells.

Examples of acids for the formation of the non-toxic, pharmaceutically acceptable acid addition salts are inorganic acids such as hydrochloric acid, hydrobromic acid and organic acids such as, hydroiodic acid, nitric acid, sulfuric acid, phosphoric acid, propionic acid, formic acid, benzoic acid, maleic acid, fumaric acid, succinic acid, tartaric acid, citric acid, oxalic acid, glyoxylic acid, aspartic acid, alkanesulfonic acid such as methane sulfonic acid and arylsulfonic acids such as benzene sulfonic acid.

Among the preferred compounds of formula I are those wherein R is —NH—CO—NH$_2$, those wherein R is —NH—CO—CH$_3$ and those wherein R is —OH and their acid addition salts. Particularly preferred is 1,2-naphthoquinone-2-semicarbazone known under its international name as naftazone.

Because of these remarkable properties which allow the proliferation of endothelial cells to be accelerated and the NO synthases to be inhibited, the method can be used in the vascular domain, for example in the prevention of hypotension relating to septic shock, atheroma, arterial recurrence of stenosis (after angioplasty), in vascular protection, in transplants and vascular protheses, in cerebral protection during a "stroke", or in the treatment of pain, as an antioedematous agent by lowering the capillary permeability, in the treatment of migraine by closing the cerebral arteriovenous shunts, in pathological processes involving micro-circulation (in ophthalmology, in the study of diabetes) as in vascularities (in particular medicinal) and in all healing and tissue repair processes.

The usual dose, which is variable depending on the product used, the patient treated and the illness in question, can be 0.01 to 1.3 mg/kg per day.

The compounds may be in the form of tablets, dragees, capsules, granules, suppositories and injectable solutions or suspensions. Orally, rectally or parenterally.

Examples of the inert pharmaceutical carriers are talc, gum arabic, lactose, starch, magnesium stearate, cocoa butter, aqueous or non-aqueous vehicles, fatty substances of animal or vegetable origin, various wetting, dispersing or emulsifying agents, preservatives.

The compounds of formula I are known and may be prepared as described in the literature and French Patent No. 2,103,504.

In the following examples, there are described several preferred embodiments to illustrate the invention. However, it is to be understood that the invention is not intended to be limited to the specific embodiments.

EXAMPLE 1

Tablets were prepared containing 10 mg of naftazone and sufficient excipient of lactose, starch, talc, and magnesium stearate for a tablet of 150 mg.

EXAMPLE 2

An injectable solute was prepared containing 5 mg of naftazone and sterile aqueous excipient s.q.f. of 2 ml.

EXAMPLE 3

8.6 g of naftazone were introduced into 200 ml of acetic anhydride and after heating for 10 hours at 140° C., the reaction medium was cooled down and filtered. The precipitate was extracted with chloroform, followed by evaporation to dryness, taking up with ethanol, passing through activated charcoal, filtration and slow crystallization to obtain 5.1 g of product corresponding to formula I with R=—NH—CO—CH$_3$ as a yellow ochre micro-crystalline powder melting at 137°–138° C.

PHARMACOLOGICAL STUDY

I. In vitro study of the proliferation of human endothelial cells of the saphenous vein The mitogenic properties of naftazone were evaluated on human endothelial cells of saphenous vein in culture under standard conditions. Naftazone, at concentrations of between $10^{-5}$M and $10^{-7}$M, accelerated the proliferation of endothelial cells seeded at low density by a factor of 2 at maximum in comparison to the control (without naftazone). At confluence, the cell density remained slightly increased (approximately 20%). On the other hand, in the presence of optimal concentrations of serum, the difference in cell density between the control and the samples containing naftazone was less clear.

In conclusion, under the test conditions, the effect of the naftazone remained generally less than or equal to that induced by FGFS's, but at confluence, the cell density in the presence of FGFS factors was clearly greater than that obtained with naftazone, in comparison to the control.

II. Study of inhibition of the constitutive NO synthase of vascular endothelial cells Naftazone was the subject of studies carried out on rings 3 to 4 mm in length of the aorta abdominalis of a CD rat weighing 200–250 g (Charles River, France) and the femoral vein of a New-Zealand rabbit weighing 2–2.5 kg (Charles River, France).

The rings were placed in an organ chamber (25 ml, Phymep, France) in a Krebs-Ringer solution. This solution was subjected to permanent tonometry by a gaseous mixture of 95% $O_2$-5% $CO_2$, at pH 7.40 and thermostatically controlled at 37° C. The isometric force developed by rings was measured by tension sensors (Phymep, France). The rings were brought to their optimal point of tension-length relationship by repeated stimulations using 40 mM of KCl. Pharmacological studies were carried out after rinsing and an equilibrium period of 45 minutes. When the pharmacological response of the vessel was studied without endothelium, the latter was eliminated by rubbing the interior of the vessel using dissection forceps. The absence of endothelium was verified by the absence of relaxation of the vessel induced by $10^{-6}$M ACh after contraction with $10^{31}$ $^7$M NAD. The contractions were expressed as a % of the maximum contraction with 60 mN KCl, the relaxations were expressed as a % of the contraction with $10^{-5}$M NAD or $10-7$M PGF2.

The following pharmacological properties were observed:

1. naftazone ($10^{-6}$M–$10^{-4}$M) significantly increased the basal tonus of the aortic rings of a rat and the femoral vein of a rabbit.

2. Naftazone ($10^{-6}$M–$10^{-4}$M) potentialized the contractions obtained with NAD ($10^{-9}$M–$10^{-5}$M) and with 5HT ($10^{-9}$M–$10^{-5}$M) on the aorta of a rat in a significant and dose-dependent manner. This potentialization disappeared in the absence of endothelium.

3. On aortic rings contracted with NAD ($10^{-5}$M), naftazone ($10^{-6}$ M–$10^{-4}$M) inhibited in a significant and dose relaxation with ACh ($10^{-5}$M). This inhibition reached 60 to 80% for naftazone ($10^{-5}$M) for a relaxation obtained with ACh ($10^{-5}$M). This inhibition was comparable in kinetics and in amplitude to that obtained with N-nitro-L-arginine ($10^{-6}$M) (a powerful inhibitor of NO synthases. On aortic rings contracted with PFG2 ($2.10^{-6}$M) in the presence of Indomethacin ($10^{-5}$M) and ketanserin ($10^{-5}$M), naftazone ($10^{-6}$M–$10^{-5}$M) in a significant and dose-dependent manner ($10^{-6}$M–$10^{-4}$M).

4. On aortic rings contracted with NAD ($10^{-7}$M) or with PGF2 ($2.10^{31}$ $^6$M) in the presence of Indomethacin ($10^{-5}$M), naftazone inhibited the relaxation obtained with calcium ionophore A23187 ($10^{-6}$M–$10^{-4}$M) in a significant and dose-dependent manner ($10-6$M–$10^{-4}$M).

5. The inhibition of endothelium relaxation dependent on ACh, 5HT and A23187 obtained with naftazone ($10^{-5}$M) was completely removed by L-Arginine ($9.10^{-4}$M).

6. Naftazone ($10^{-5}$M) significantly inhibited the hyporeactivity with NAD ($10^{-9}$M–$10^{-5}$M) obtained after incubation of the aortic rings of a rat for 3 hours in the presence of lipopolysaccharides E. coli 011B4 (10 μm/ml). This effect was comparable with that obtained with N-nitro-L-arginine ($10^{-5}$M).

7. Naftazone ($10^{-5}$M) potentialized the contraction with NAD ($10^{-9}$M–$10^{-5}$M) obtained on rings of the femoral vein of a rabbit and inhibited the relaxation with ACh ($10^{-9}$M–$10^{-5}$M).

In conclusion, increase of the basal tonus, potentialization of the vasoactive effects of noradrenaline, serotonin, inhibition of endothelium relaxations dependent on acetylcholine, serotonin and calcium ionophore A23187, removal of the inhibition of endothelium relaxations dependent on L-arginine, inhibition of the hyporeactivity with noradrenaline induced by the bacterial endotoxin, classify naftazone as an inhibitor of constitutive NO synthases and induced NO synthase.

Various modifications of the method of the invention may be made without departing from the spirit or scope thereof and it is to be understood that the invention is intended to be limited only as defined in the appended claims.

What is claimed is:

1. A method of accelerating the proliferation of endothelial cells with inhibition of NO synthases in warm-blooded animals comprising administering to warm-blooded animals an amount of at least one compound selected from the group consisting of a β-naphthoquinone of the formula

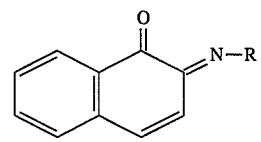

wherein R is selected from the group consisting of —NH—CO—NH$_2$, —NH—CO—CH$_3$ and —OH and their non-toxic, pharmaceutically acceptable acid addition salts in an amount sufficient to accelerate the proliferation of endothelial cells.

2. The method of claim 1 wherein R is —NH—CO—NH$_2$.

3. The method of claim 1 wherein R is —NH—CO—CH$_3$.

4. The method of claim 1 wherein R is —OH.

5. The method of claim 1 wherein the compound used is 1,2-naphthoquinone-2-semicarbazone.

* * * * *